US00PP19717P2

(12) United States Plant Patent
Kanaya et al.

(10) Patent No.: US PP19,717 P2
(45) Date of Patent: Feb. 17, 2009

(54) ***PETUNIA* PLANT NAMED 'SUNSURFHOMI'**

(50) Latin Name: *Petunia×hybrida*
Varietal Denomination: Sunsurfhomi

(75) Inventors: Takeshi Kanaya, Shiga (JP); Yasuko Isobe, Shiga (JP); Kazunari Iwaki, Kanagawa (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/077,221

(22) Filed: Mar. 17, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'Sunsurfhomi', characterized by its trailing plant habit; vigorous growth habit; freely branching and flowering plant habit; long flowering period; small-sized white-colored flowers; and good garden performance.

1 Drawing Sheet

Botanical designation: *Petunia×hybrida.*
Cultivar denomination: 'Sunsurfhomi'.

BACKGROUND OF THE INVENTION

The present invention relates to a new and distinct cultivar of *Petunia,* botanically known as *Petunia×hybrida* and hereinafter referred to by the name 'Sunsurfhomi'.

The new *Petunia* is a product of a planned breeding program conducted by the Inventors in Higashiomi, Shiga, Japan. The objective of the breeding program is to create new *Petunia* cultivars with attractive foliage and flower coloration.

The new *Petunia* originated from a cross-pollination made by the Inventors in September, 2003 in Higashiomi, Shiga, Japan of a proprietary selection of *Petunia×hybrida* identified as code number PS56-3, not patented, as the female, or seed, parent with a proprietary selection of *Petunia×hybrida* identified as code number PS143-1, not patented, as the male, or pollen, parent. The new *Petunia* was discovered and selected by the Inventors as a single flowering plant within the progeny of the stated cross-pollination in a controlled environment in Higashiomi, Shiga, Japan.

Asexual reproduction of the new *Petunia* by terminal cuttings in a controlled environment in Higashiomi, Shiga, Japan since September, 2005, has shown that the unique features of this new *Petunia* are stable and reproduced true to type in successive generations.

SUMMARY OF THE INVENTION

The cultivar Sunsurfhomi has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfhomi'. These characteristics in combination distinguish 'Sunsurfhomi' as a new and distinct cultivar of *Petunia:*

1. Trailing plant habit.
2. Vigorous growth habit.

3. Freely branching and flowering plant habit.
4. Long flowering period.
5. Small-sized white-colored flowers.
6. Good garden performance.

Plants of the new *Petunia* can be compared to plants of the female parent selection. Plants of the new *Petunia* differ from plants of the female parent selection in the following characteristics:

1. Plants of the new *Petunia* are more trailing than plants of the female parent selection.
2. Plants of the new *Petunia* have larger flowers than plants of the female parent selection.

Plants of the new *Petunia* can be compared to plants of the male parent selection. Plants of the new *Petunia* differ from plants of the male parent selection in the following characteristics:

1. Plants of the new *Petunia* have larger flowers than plants of the male parent selection.
2. Plants of the new *Petunia* and the male parent selection differ in flower color as plants of the male parent selection have soft pink-colored flowers.

Plants of the new *Petunia* can also be compared to plants of the cultivar Keiwhihus, disclosed in U.S. Plant Pat. No. 18,089. In side-by-side comparisons conducted in Higashiomi, Shiga, Japan, plants of the new *Petunia* and the cultivar Keiwhihus differed in the following characteristics:

1. Plants of the new *Petunia* had shorter internodes than plants of the cultivar Keiwhihus.
2. Plants of the new *Petunia* had smaller flowers than plants of the cultivar Keiwhihus.
3. Flowers of plants of the new *Petunia* and the cultivar Keiwhihus differed slightly in color as flowers of plants of the cultivar Keiwhihus had yellowish white-colored flowers.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a top perspective view of a typical flowering plant of 'Sunsurfhomi' grown in a container.

The photograph at the bottom of the sheet is a close-up view of typical flowers of 'Sunsurfhomi'.

DETAILED BOTANICAL DESCRIPTION

The aforementioned photographs and following observations, measurements and values describe plants grown in Higashiomi, Shiga, Japan, under commercial practice during the summer in an outdoor nursery day temperatures averaging 23° C., and night temperatures averaging 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Petunia×hybrida* cultivar Sunsurfhomi.

Parentage:

*Female, or seed, parent.*—Proprietary selection of *Petunia×hybrida* identified as code number PS56-3, not patented.

*Male, or pollen, parent.*—Proprietary selection of *Petunia×hybrida* identified as code number PS143-1, not patented.

Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous, fleshy; light brown in color.

*Rooting habit.*—Freely branching.

Plant description:

*Plant and growth habit.*—Trailing plant habit. Freely branching habit with about seven lateral branches developing per plant; pinching enhances lateral branch development. Vigorous growth habit.

*Plant height.*—About 14.5 cm.

*Plant diameter.*—About 65.4 cm.

Lateral branch description:

*Length.*—About 39.7 cm.

*Diameter.*—About 2.2 mm.

*Internode length.*—About 1.3 cm.

*Strength.*—Strong, flexible.

*Aspect.*—Decumbent.

*Texture.*—Pubescent.

*Color.*—Close to 144A.

Foliage description:

*Arrangement.*—Before flowering, alternate, simple; after flowering, opposite, simple.

*Length.*—About 4.6 cm.

*Width.*—About 1.9 cm.

*Shape.*—Elliptic.

*Apex.*—Obtuse.

*Base.*—Cuneate.

*Margin.*—Entire.

*Texture, upper and lower surfaces.*—Pubescent.

*Venation pattern.*—Pinnate; reticulate.

*Color.*—Developing and fully expanded foliage, upper surface: Close to 144A; venation, close to 145A. Developing and fully expanded foliage, lower surface: Close to 146B; venation, close to 145A.

*Petiole.*—Length: About 8 mm. Diameter: About 1.8 mm. Texture, upper and lower surfaces: Sparsely pubescent. Color, upper and lower surfaces: Close to 145A.

Flower description:

*Flower arrangement and habit.*—Single salverform flowers arising from leaf axils. Freely flowering habit with usually about 51 open flowers per plant. Flowers face upright or outwardly. Flowers not fragrant.

*Natural flowering season.*—Plants of the new *Petunia* initiate and develop flowers about three to four weeks after planting. Long flowering period; flowering commences naturally during the spring and plants flower continuously throughout the summer until late autumn in Japan. Flowers not persistent.

*Flower longevity.*—Individual flowers last about seven to ten days on the plant.

*Flower diameter.*—About 3.7 cm.

*Flower length (depth).*—About 3.5 cm.

*Throat diameter.*—About 8.2 mm.

*Tube diameter, base.*—About 1.9 mm.

*Tube length.*—About 2.3 cm.

*Flower bud.*—Shape: Cylindrical. Length: About 2.6 cm. Diameter: About 4.9 mm. Color: Close to 145C.

*Corolla.*—Arrangement: Five petals fused at the base and opening into a flared trumpet. Petal length from throat: About 1.5 cm. Petal width: About 1.7 cm. Petal shape: Spatulate. Petal apex: Mucronate. Petal margin: Entire. Petal texture, upper and lower surfaces: Smooth, glabrous; velvety. Throat texture: Smooth, glabrous. Tube texture: Pubescent. Color: Petal, when opening and fully opened, upper surface: Close to 155C. Petal, when opening and fully opened, lower surface: Close to 155C; venation, close to 145A. Throat: Close to 155C. Tube: Close to 155C.

*Calyx.*—Arrangement: One star-shaped calyx tube with five sepals fused at the base per flower. Sepal length: About 1.1 cm. Sepal width: About 1.8 mm. Sepal shape: Lanceolate. Sepal apex: Obtuse. Sepal margin: Entire. Sepal texture, upper and lower surfaces: Pubescent. Color, upper and lower surfaces: Close to 144A.

*Peduncles.*—Length: About 1.7 cm. Diameter: About 0.9 mm. Strength: Strong. Texture: Pubescent. Color: Close to 144A.

*Reproductive organs.*—Stamens: Quantity/arrangement: Five per flower. Stamen length: About 8.3 mm to 16.9 mm. Anther shape: Ellipsoidal. Anther size: About 1.7 mm by 1.8 mm. Anther color: Close to 150D. Pollen amount: Moderate. Pollen color: Close to 155A. Pistils: Quantity: One per flower. Pistil length: About 1.3 cm. Style color: Close to 145B. Stigma shape: Transversely ellipsoidal. Stigma color: Close to 145B. Ovary color: Close to 143C.

*Seed/fruit.*—Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Sunsurfhomi' as illustrated and described.

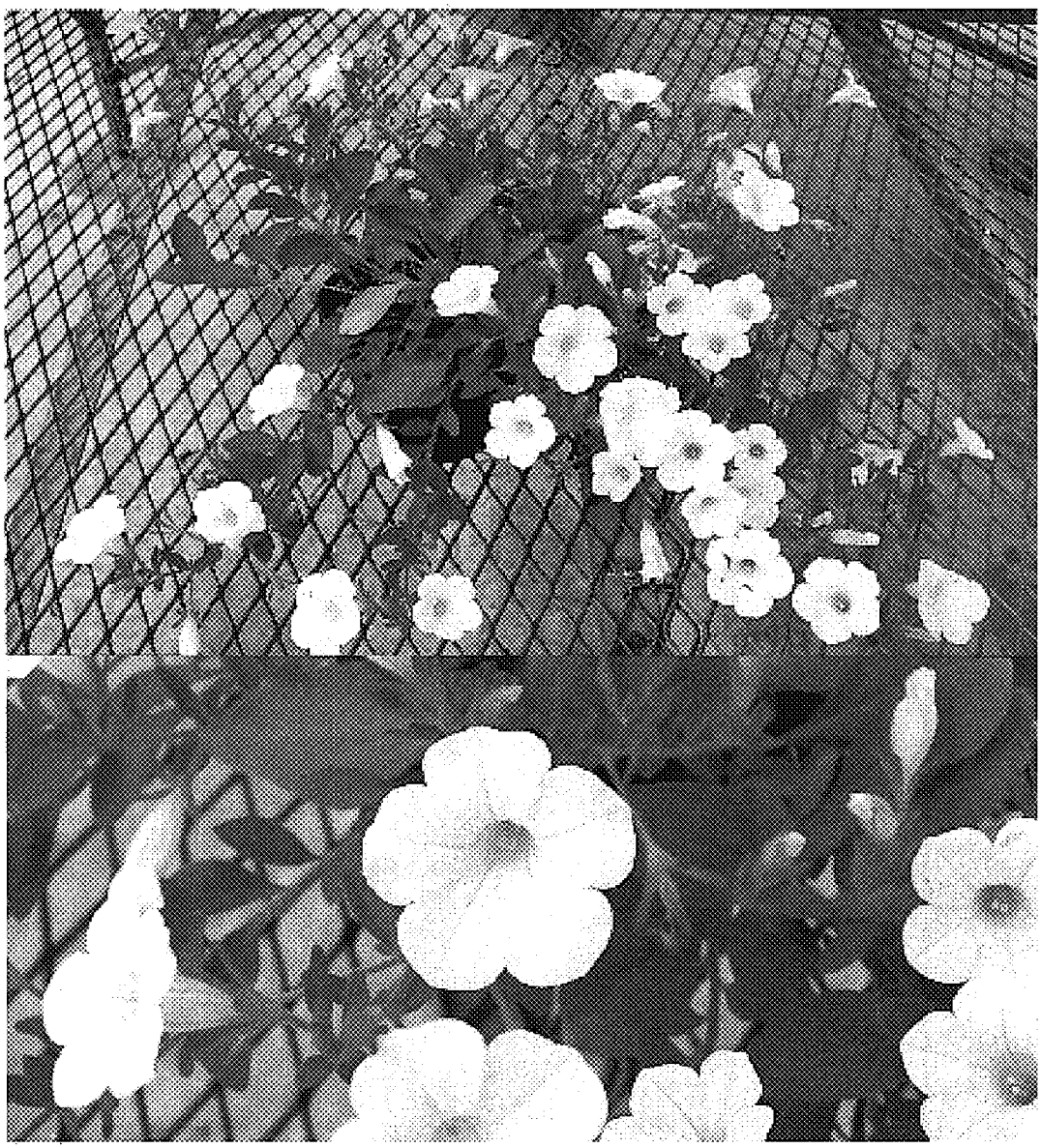

* * * * *